(12) United States Patent
Kim et al.

(10) Patent No.: US 6,278,761 B1
(45) Date of Patent: Aug. 21, 2001

(54) METHOD OF ESTABLISHING RANGE OF SOMATIC FAT BY GAUSSIAN FUNCTION APPROXIMATION IN COMPUTERIZED TOMOGRAPHY

(75) Inventors: Seung Hwan Kim; Seon Hee Park; Hyeon Bong Pyo, all of Daejon-Shi (KR)

(73) Assignee: Electronics and Telecommunications Research Institute, Daejon-Shi (KR)

( * ) Notice: Subject to any disclaimer, the term of this patent is extended or adjusted under 35 U.S.C. 154(b) by 0 days.

(21) Appl. No.: 09/419,486

(22) Filed: Oct. 15, 1999

(30) Foreign Application Priority Data

Oct. 28, 1998 (KR) .................................................. 98-45433

(51) Int. Cl.[7] ...................................................... A61B 6/03
(52) U.S. Cl. ................................................. 378/8; 378/901
(58) Field of Search ...................................... 378/4, 8, 901

(56) References Cited

U.S. PATENT DOCUMENTS

| | | | |
|---|---|---|---|
| 4,831,527 | 5/1989 | Clark | 600/553 |
| 5,068,788 | * 11/1991 | Goodenough et al. | 382/131 |
| 5,415,176 | 5/1995 | Sato et al. | 600/547 |
| 5,870,697 | * 2/1999 | Chandler et al. | 702/179 |

OTHER PUBLICATIONS

Kvst et al., Total and visceral adipose–tissue volumes derived from measurements with computed tomography in adult men and women: predictive dquations[1–3], 1988, pp. 1351–1361.

Grauer et al., Quantificatio of body fat distibution in the abdomen using computed tomography[1, 2], Apr. 1984, pp. 631–637.

Borkan et al., Assessment of abdominal fat content by computed tomography[1–3], Jul. 1982, pp. 172–177.

* cited by examiner

*Primary Examiner*—David V. Bruce
(74) *Attorney, Agent, or Firm*—Cohen, Pontani, Lieberman & Pavane

(57) ABSTRACT

The present invention relates to a method of establishing a range of somatic fat by Gaussian function approximation in a computerized tomography to automatically establish through Gaussian function approximation by using least square method the range of somatic fat which is used at the time of measuring the somatic fat by using the computerized tomography, comprising the steps of separating an intra-abdominal cavity and an extra-abdominal cavity at the time of measuring amounts of subcutaneous fat and intra-abdominal cavity fat by using the computerized tomography, preparing a histogram of Hounsfield values of the separated intra-abdominal cavity and extra-abdominal cavity, approximating the prepared histogram to Gaussian function by using least square method and establishing the range of somatic fat by using a position and width of peak of the obtained Gaussian function.

4 Claims, 7 Drawing Sheets

METHOD OF ESTABLISHING RANGE OF SOMATIC FAT BY GAUSSIAN FUNCTION APPROXIMATION IN COMPUTERIZED TOMOGRAPHY

BACKGROUND OF THE INVENTION

1. Field of the Invention

The present invention relates to a method of establishing range of somatic fat by Gaussian function approximation in computerized tomography which can automatically establish the range of somatic fat, which is used at the time of measuring the somatic fat by using the computerized tomography, using Gaussian function approximation by least square method.

2. Information Disclosure Statement

The importance of measurement of somatic fat has increased day by day in connection with fatness, and various methods of measurement of somatic fat have been suggested and used.

Although a method of measuring fatness degree by using ratio of height and weight is well known, it has a disadvantage that the correlation of ratio of height and weight with the amount of actual somatic fat is not strong. In addition, there is a method of measuring the amount of somatic fat by measuring conductivity, however, it has a disadvantage that accuracy is low since a deviation of the conductivity is large according to the measurement method. Further, there is a method of measuring ratio of waist circumference and hip circumference, however, it has a disadvantage that the correlation of the ratio of waist circumference and hip circumference with the actual amount of somatic fat is not strong. Still further, there is a method of measuring thickness of subcutaneous fat by pliers, however it has a disadvantage that the degree of precision is low since the method itself is very simple and can not directly measure the amount of somatic fat.

Recently, ratio of subcutaneous fat and intra-abdominal cavity fat is used as an indication of disease connected with the fatness, and a method of separately measuring the subcutaneous fat and intra-abdominal cavity fat is required. The computerized tomography is a means which satisfies such requirement and can separately and directly measure through an image processing the amounts of subcutaneous fat and intra-abdominal fat from computerized tomography image.

The computerized tomography provides an image composed of Hounsfield values proportional to density. The Hounsfield value for the air is −1000 and that for the water is 0. Further, the Hounsfield value for a material of high density such as a bone is 1000.

The method of measuring the somatic fat from the image composed as described above is a method in which a range of Hounsfield values corresponding to the somatic fat is given and the number of pixels belonging to the range is counted.

However, there is no standard range since a reference for the range of somatic fat is vague and different ranges of somatic fat are used depending on person. In addition, since the characteristic of somatic fat varies with person and region, different range of somatic fat have to be given, however, up to now, the same value has been used in the measurement of various persons and various regions.

SUMMARY OF THE INVENTION

Therefore, an object of the present invention is to provide a method of establishing range of somatic fat by Gaussian function approximation in the computerized tomography which can solve the disadvantage described above by obtaining a histogram of Hounsfield value in computerized tomography image, approximating the histogram by Gaussian function by least square method and determining the range of somatic fat from a position and a width of a somatic fat histogram peak, to automatically establish the range of somatic fat by considering characteristics of persons and regions.

A method of establishing the range of somatic fat by Gaussian function approximation in the computerized tomography according to the present invention to accomplish the object described above comprises a step of separating an intra-abdominal cavity and an extra-abdominal cavity at the time of measuring amounts of subcutaneous fat and intra-abdominal cavity fat by using the computerized tomography, a step of preparing histograms of Hounsfield values of the separated intra-abdominal cavity and extra-abdominal cavity, a step of approximating the prepared histograms to Gaussian function by using least square method, and a step of establishing the range of somatic fat with a position and width of peak of the obtained Gaussian function.

BRIEF DESCRIPTION OF THE DRAWINGS

The above object, and other features and advantages of the present invention will become more apparent by describing the preferred embodiment thereof with reference to the accompanying drawings, in which.

Similar reference characters refer to similar parts in the several views of the drawings.

DETAILED DESCRIPTION OF PREFERRED EMBODIMENT

A detailed description of the present invention will be given below with reference to the accompanying drawings.

Figure 1A:
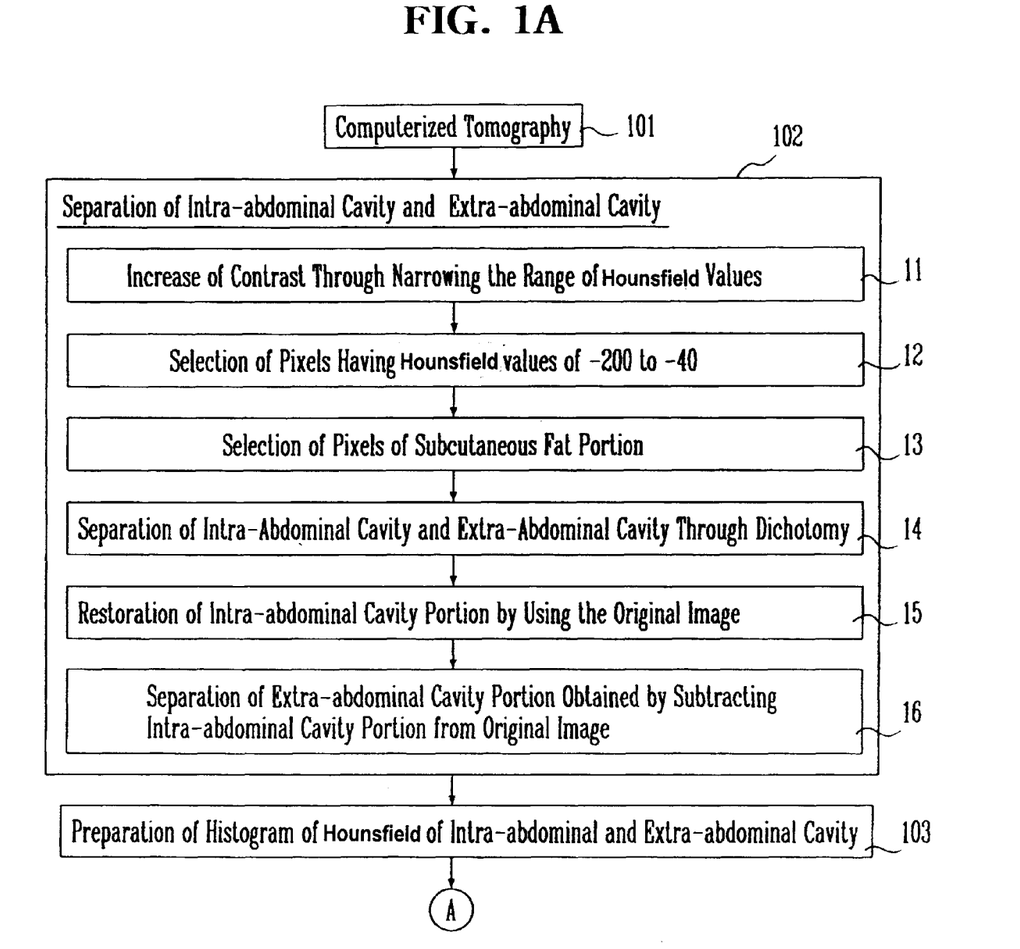
FIGS. 1A and 1B are flow diagrams to illustrate the method of establishing the range of somatic fat by Gaussian function approximation in computerized tomography according to the present invention.
Figure 1B:
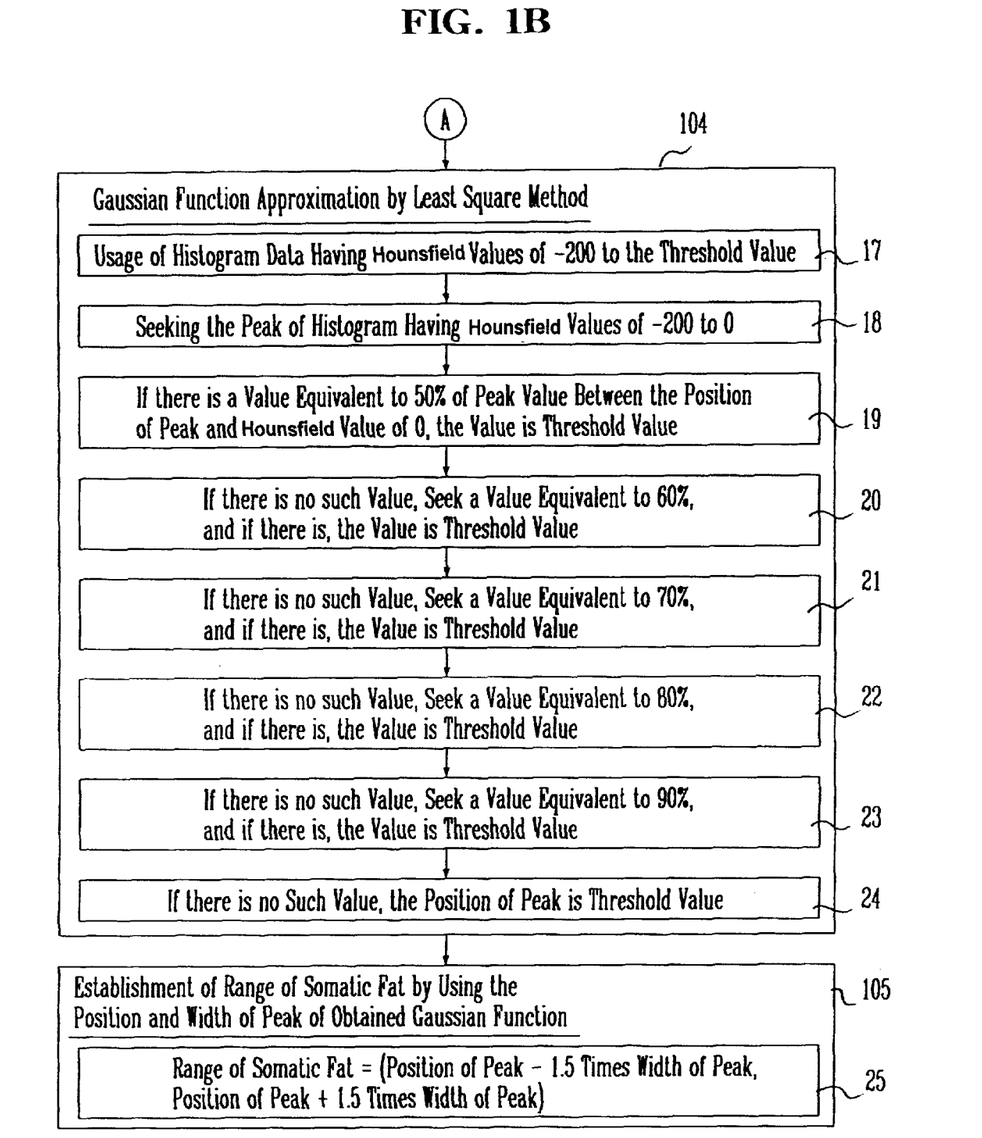

FIGS. 1A and 1B are flow diagrams to illustrate a method of establishing the range of somatic fat by Gaussian function approximation in computerized tomography according to the present invention and will be explained in detail with reference to FIGS. 2 to 10.

Figure 2:
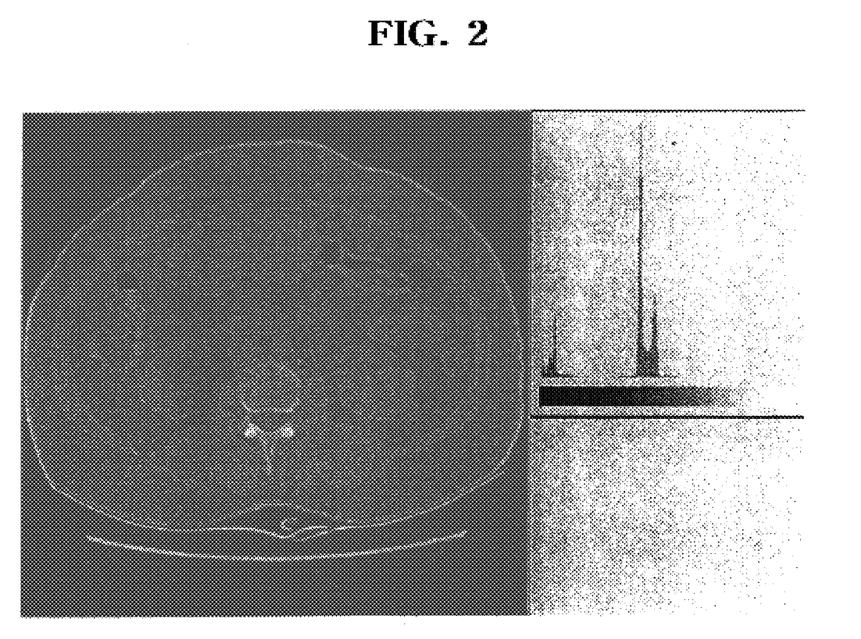
FIG. 2 shows a computerized tomography image and its histogram.

First, a tomography image of a person of whom the somatic fat is to be measured is obtained by means of the computerized tomography as shown in the flow diagram of the present invention shown in FIG. 1A (101). An example of computerized tomography image is shown in FIG. 2. The tomography image thus obtained is an image composed of Hounsfield values proportional to density. The Hounsfield value is given as −1000 for the air, 0 for the water and 1000 for a material of high density such as bone.

Figure 3:
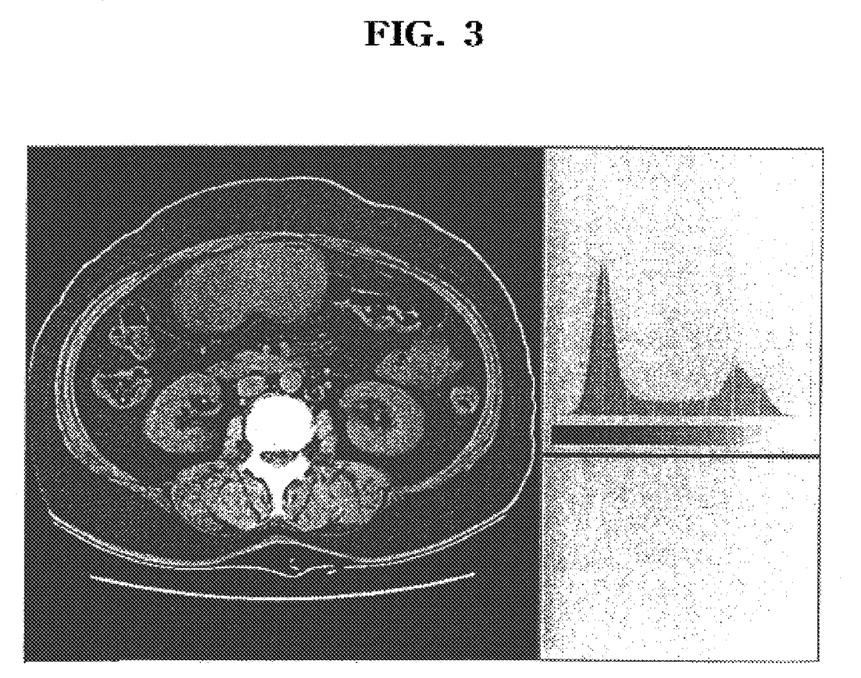
FIG. 3 shows a computerized tomography image and its histogram in which contrast is raised by narrowing the range in Hounsfield values.
Figure 4:
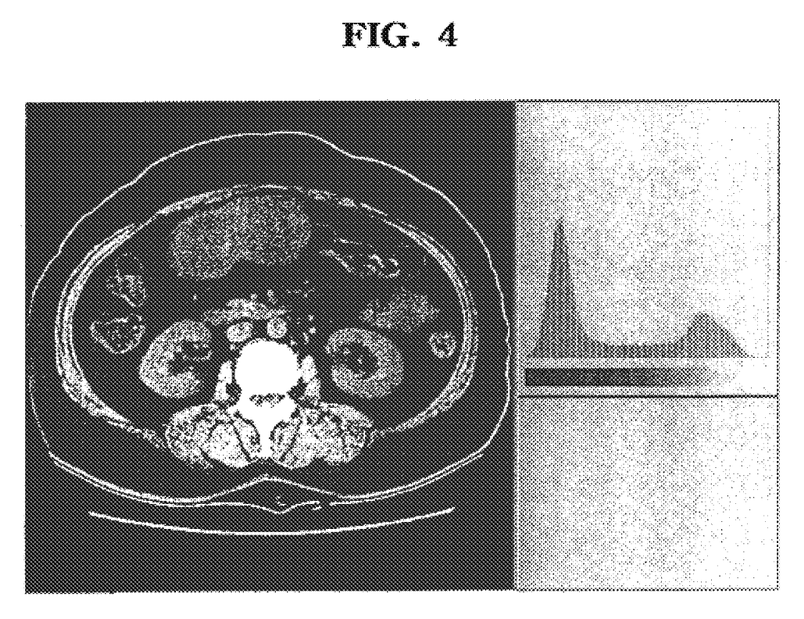
FIG. 4 shows a computerized tomography image and its histogram after converting pixels having Hounsfield values between −200 and −40 into the same value.
Figure 5:
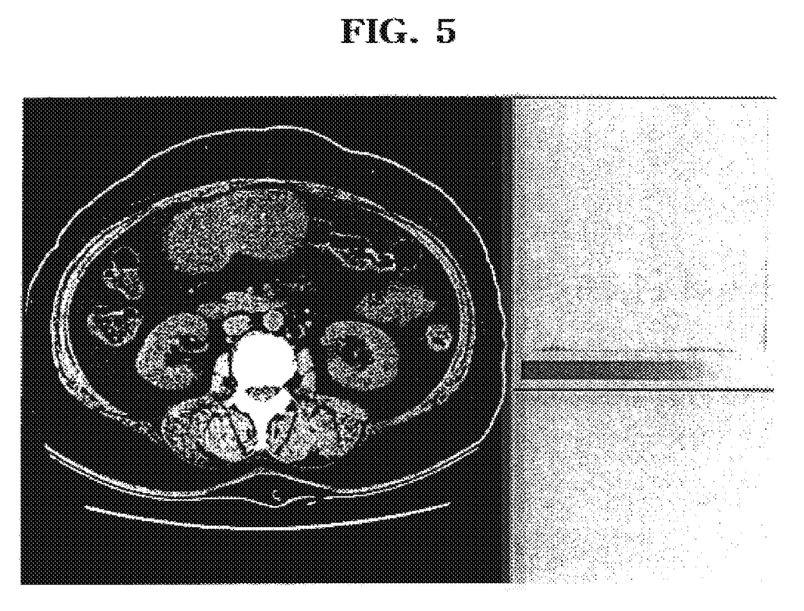
FIG. 5 shows a computerized tomography image and its histogram after separating a subcutaneous part into pixel portions having same Hounsfield values.
Figure 6:
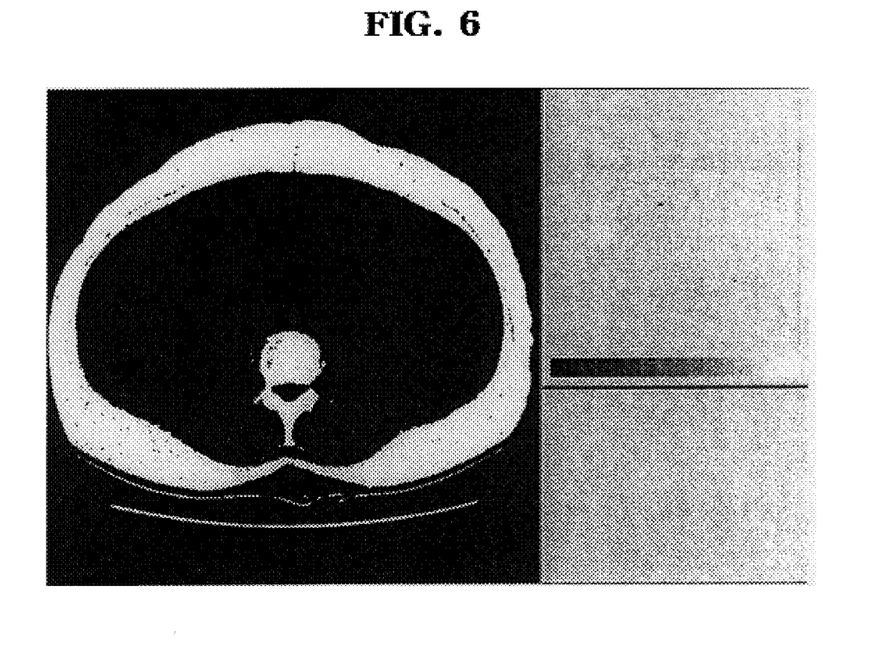
FIG. 6 shows a computerized tomography image and its histogram after separating an intra-abdominal cavity and a subcutaneous part by using dichotomy.
Figure 7:
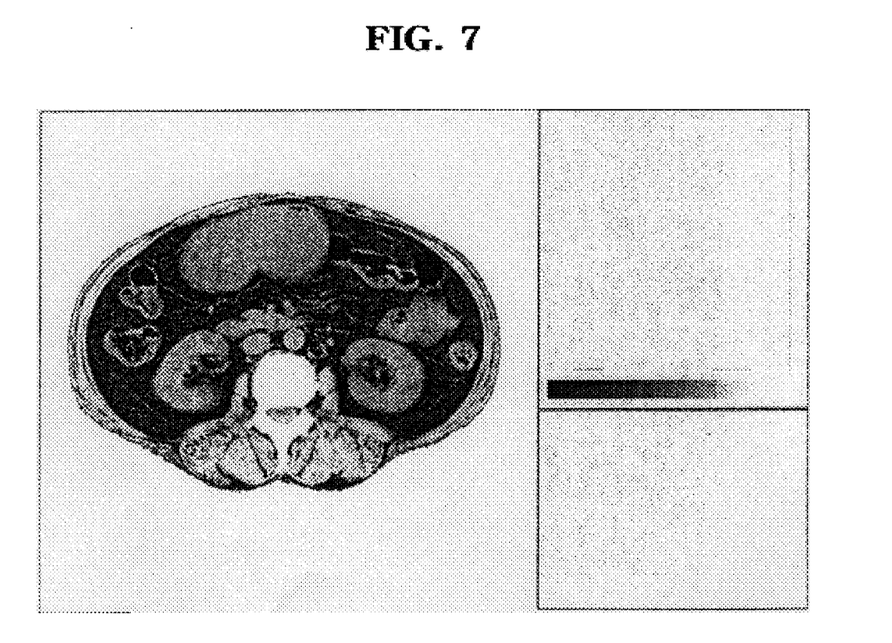
FIG. 7 shows a computerized tomography image and its histogram after restoring intra-abdominal cavity portion by using an original image.

The abdominal cavity portion and the subcutaneous portion are separated in the computerized tomography image to separately measure the amounts of intra-abdominal cavity fat and subcutaneous fat (102). An image of high contrast is obtained as shown in FIG. 3 by narrowing the range of Hounsfield values from −1000 to 1000 to −200 to 100 to separate the abdominal cavity and the subcutaneous portion (11). In thus obtained image, the pixels having Hounsfield values of −200 to −40 are painted with same color as shown in FIG. 4 (12). In this way, the subcutaneous fat portion is combined into one lump (13). The subcutaneous fat portion is separated into a portion composed of same values so as to separate the abdominal cavity and the subcutaneous portion as shown in FIG. 5. The intra-abdominal cavity and the subcutaneous portion are completely separated by performing the dichotomy on the image obtained as described above as shown in FIG. 6 (14). If the intra-abdominal cavity portion is restored from the separated image by using the original image, the image of the intra-abdominal cavity alone is obtained as shown in FIG. 7 (15). The image of subcutaneous portion can be obtained if the image of interior alone obtained in FIG. 7 is subtracted from the original image (16).

Figure 8:
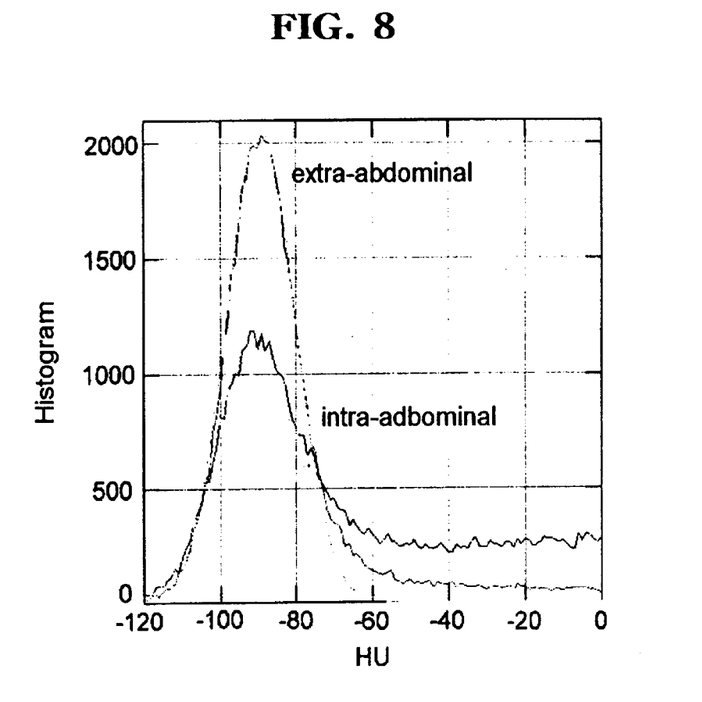
FIG. 8 shows histograms of Hounsfield values of intra-abdominal cavity and subcutaneous part.

The histograms of Hounsfield values are obtained from the image of intra-abdominal cavity and the image of subcutaneous portion in the method described above to establish the ranges of subcutaneous fat and the intra-abdominal cavity fat (103). The histogram indicates the number of pixels equivalent to each Hounsfield values, and the histograms of the intra-abdominal cavity and the extra-abdominal cavity are shown in FIG. 8. As shown in FIG. 8, the histograms of the intra-abdominal cavity and the extra-abdominal cavity each have one peak. The position of peak indicates the Hounsfield value equivalent to each fat.

This peak is approximated by Gaussian function by using least square method (104). The reason of approximation by Gaussian function is because the somatic fat is not composed of pure fat but is mixed with various different foreign materials such as muscle, air and water, etc. That is, assuming that different foreign materials are mixed with the pure fat, it is anticipated that the density distribution of somatic fat has a normal distribution centered at a certain density. That is, it is anticipated that the density distribution of somatic fat will appear as Gaussian function.

The range of data used in the Gaussian function approximation is determined by two thresholds. Lower threshold is set as Hounsfield value of −200 (17). Upper threshold is set by method described below. First, a peak is sought at Hounsfield value between −200 and 0 (18). If the peak is found, a value equivalent to 50% of peak value is sought by increasing Hounsfield value from the position of peak to 0. If there is an equivalent value, it is used as the upper threshold (19). If there is no equivalent value, a value equivalent to 60% of peak is sought in the same way. If there is an equivalent value, it is used as the upper threshold (20). If there is no value equivalent to 60%, a value equivalent to 70% is sought (21), if there is no value equivalent to 70%, a value equivalent to 80% is sought (22), if there is no value equivalent to 80%, a value equivalent to 90% is sought (23). If there is no value equivalent to 90%, the position of peak is used as upper threshold (24).

The histogram data are approximated to Gaussian function by least square method. The approximated Gaussian function is shown in FIG. 8. As shown in FIG. 8, the histogram is well approximated to Gaussian function.

By using the peak position and peak width of Gaussian function, the range of somatic fat is set to be (position of peak−1.5 times width of peak, position of peak+1.5 times width of peak) (25) (105).

As described above, a detailed embodiment of the present invention is shown, where the numbers may vary depending upon the computerized tomography image. The important point in the present invention is to set the range of somatic fat at the time of measuring the somatic fat in the computerized tomography image, however, up to now, it has been set in a unique way to be a particular range, for example, −200 to −50 or −250 to −10. In addition, the various values for setting were used and there was no standard establishing method. In the present invention, as a way of solving such problems, a method has been proposed of establishing the range of somatic fat by using the peak position and width obtained by approximating the histogram of somatic fat to Gaussian function.

Figure 9:
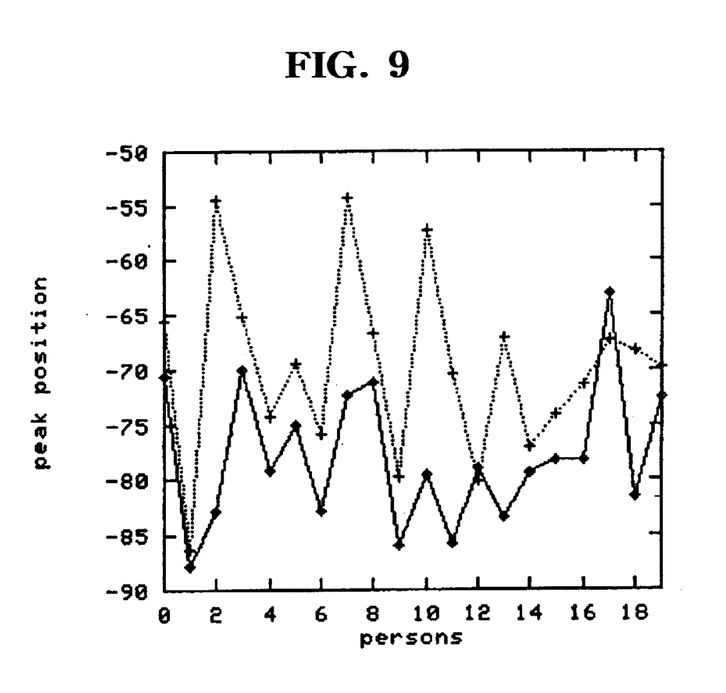
FIG. 9 shows a peak position of Gaussian function of intra-abdominal cavity(+) and subcutaneous part(✧) for various persons.
Figure 10:
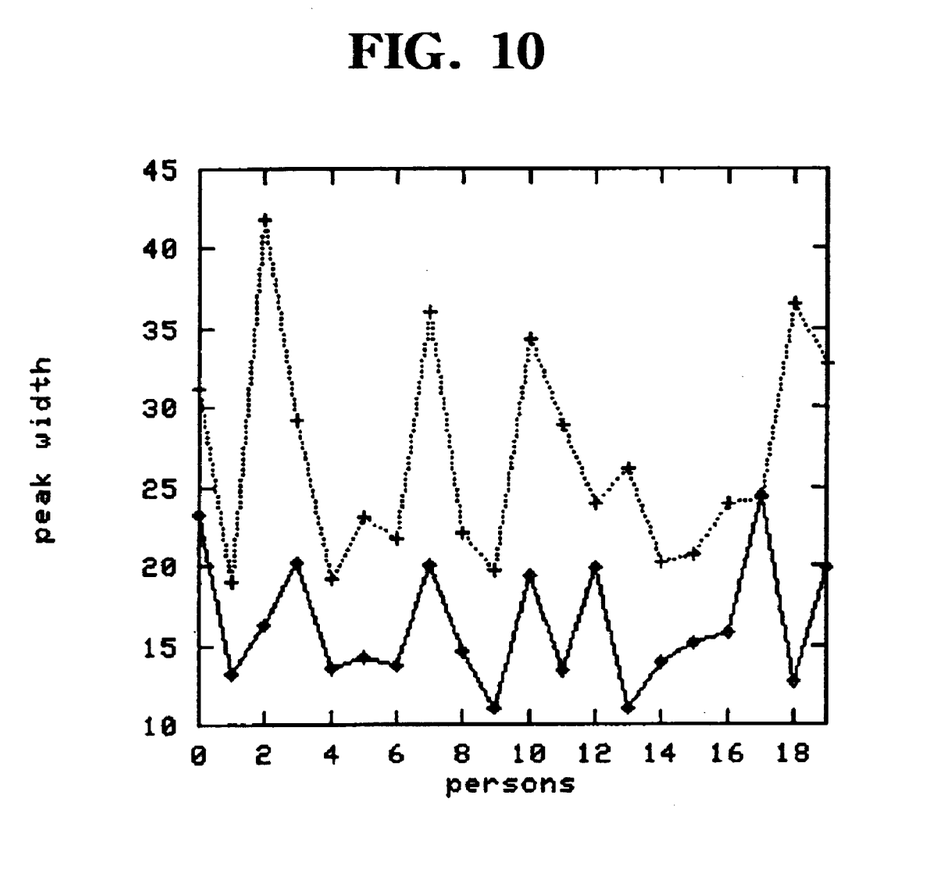
FIG. 10 shows a peak width of Gaussian function of intra-abdominal cavity(+) and subcutaneous part (✧)for various persons.

By using the method described above, the range of somatic fat can be established in consideration of the characteristics of somatic fat according to persons and portions. In FIG. 9 is shown a position of peak obtained by Gaussian function approximation of intra-abdominal cavity fat and subcutaneous fat according to persons. As shown there, the position of peak varies with person. That is, it can be seen that the density of somatic fat varies with person. In FIG. 10 widths of peak obtained by Gaussian function approximation of intra-abdominal cavity fat and subcutaneous fat are shown according to persons. As shown there, the width of peak varies with person. That is, it can be seen that the distribution of density of somatic fat varies with person. In addition, as shown in FIGS. 9 and 10, the position and width of peak are different for subcutaneous fat and intra-abdominal cavity fat. That is, the characteristic of somatic fat varies with portions.

The foregoing description, described in its preferred embodiment with a certain degree of particularity, is only illustrative of the principles of the present invention. It is to be understood that the present invention is not to be limited to the preferred embodiments disclosed and illustrated herein. Accordingly, all expedient variations that may be made within the scope and spirit of the present invention are to be encompassed as further embodiments of the present invention.

What is claimed is:

1. A method of establishing a range of somatic fat by Gaussian function approximation in the computerized tomography, comprising the steps of:

separating an intra-abdominal cavity and an extra-abdominal cavity at the time of measuring amounts of subcutaneous fat and intra-abdominal cavity fat by using the computerized tomography;

preparing a histogram of Hounsfield values of said separated intra-abdominal cavity and extra-abdominal cavity;

approximating the prepared histogram to Gaussian function by using least square method; and establishing the range of somatic fat by using a position and width of peak of said obtained Gaussian function.

2. The method of claim 1, wherein said step of separating the intra-abdominal cavity and extra-abdominal cavity comprises:

a step of obtaining an image of high contrast by narrowing the range of Hounsfield values;

a step of selecting pixels having Hounsfield values of −200 to −40 from said obtained image;

a step of selecting pixels of subcutaneous fat portion;

a step of completely separating said intra-abdominal cavity and extra-abdominal cavity by dichotomy;

a step of restoring said intra-abdominal cavity portion from said separated image by using an original image; and a step of restoring by using the original image said extra-abdominal cavity portion obtained by subtracting said intra-abdominal cavity portion from said separated image.

3. The method of claim 1, further comprising:

a step of seeking the peak of histogram having the Hounsfield values of −200 to 0, the histogram data having Hounsfield values of −200 to a threshold value being used as the histogram which is used at the time of approximating Gaussian function by using least square method; and a step of, if the peak is found, seeking a value equivalent to 50% of peak value between the position of said found peak and the Hounsfield value of 0 and using the found value as the threshold value, using 60% if there is no value equivalent to 50%, using 70% if there is no value equivalent to 60%, using 80% if there is no value equivalent to 70%, using 90% if there is no value equivalent to 80%, and using the position of the peak as the threshold value if there is no value equivalent to 90%.

4. The method of claim 1, wherein the range of somatic fat established by using the position and width of peak of the Gaussian function is composed of the range of somatic fat=(position of peak−1.5 times width of peak, position of peak+1.5 times width of peak).

* * * * *